US012527683B2

(12) United States Patent
Pepito

(10) Patent No.: US 12,527,683 B2
(45) Date of Patent: Jan. 20, 2026

(54) NON-INVASIVE URINE MANAGEMENT SYSTEMS AND METHODS

(71) Applicant: Alvin M Pepito, La Habra, CA (US)

(72) Inventor: Alvin M Pepito, La Habra, CA (US)

( * ) Notice: Subject to any disclaimer, the term of this patent is extended or adjusted under 35 U.S.C. 154(b) by 556 days.

(21) Appl. No.: 18/117,973

(22) Filed: Mar. 6, 2023

(65) Prior Publication Data

US 2023/0293338 A1 Sep. 21, 2023

Related U.S. Application Data

(60) Provisional application No. 63/319,927, filed on Mar. 15, 2022.

(51) Int. Cl.
*A61F 5/451* (2006.01)

(52) U.S. Cl.
CPC .................................... *A61F 5/451* (2013.01)

(58) Field of Classification Search
CPC ........... A61F 5/451; A61F 5/4407; A61F 5/48
See application file for complete search history.

(56) References Cited

U.S. PATENT DOCUMENTS 5,334,174 A * 8/1994 Street ...................... A61F 5/451 604/315
2002/0010446 A1* 1/2002 Maimets ................. A61F 5/451 604/355
2002/0091364 A1* 7/2002 Prabhakar ............... A61F 5/451 604/327
2004/0143229 A1* 7/2004 Easter ...................... A61F 5/451 604/322
2004/0236292 A1* 11/2004 Tazoe ...................... A61F 5/451 604/317
2005/0038374 A1* 2/2005 Williams .............. A61M 1/784 604/20
2006/0015080 A1* 1/2006 Mahnensmith ........... A61F 5/48 604/327
2006/0015081 A1* 1/2006 Suzuki .................... A61F 5/451 604/329
2007/0185465 A1* 8/2007 Campbell ............... A61F 5/451 604/347
2009/0270822 A1* 10/2009 Medeiros ................ A61F 5/451 604/347
2012/0233761 A1* 9/2012 Huang ..................... A61G 5/10 4/458
2013/0261573 A1* 10/2013 Rackley ................ A61F 5/4408 604/328

(Continued)

*Primary Examiner* — Rebecca E Eisenberg
*Assistant Examiner* — Ted Yang
(74) *Attorney, Agent, or Firm* — Shalini Venkatesh

(57) ABSTRACT

A device includes a sleeve and a malleable framework. The sleeve has a waterproof layer attached to a water-permeable layer forming a cavity, with a folded over antapex region forming a pocket. The framework has a cup and a bar, attached to first and second tubes. Bottom ends of the tubes are attached to the cup such that a continuous path for fluid flow exists between the cup, a lumen of the second tube, and a suction port at a top end of the second tube. The lumen of the first tube is closed off at the bar. The lumen of the second tube remains open as it passes through the bar to the suction port. The sleeve encloses at least a lower portion of the framework, such that the cup fits into the pocket, with lower portions of the first and second tubes lying within the sleeve cavity.

14 Claims, 4 Drawing Sheets

(56) References Cited

U.S. PATENT DOCUMENTS

| | | | | |
|---|---|---|---|---|
| 2015/0305917 | A1* | 10/2015 | Su | A61F 5/451 4/144.1 |
| 2017/0340475 | A1* | 11/2017 | Joh | A61F 5/455 |
| 2019/0216992 | A1* | 7/2019 | Rickman | A61F 13/84 |
| 2020/0276046 | A1* | 9/2020 | Staali | A61B 5/202 |
| 2022/0047410 | A1* | 2/2022 | Walthall | A61M 1/73 |
| 2022/0054295 | A1* | 2/2022 | Becker | A61M 25/002 |
| 2022/0087853 | A1* | 3/2022 | Farrar | A61F 5/455 |

* cited by examiner

NON-INVASIVE URINE MANAGEMENT SYSTEMS AND METHODS

CROSS-REFERENCE TO RELATED APPLICATIONS

This application claims priority from U.S. Provisional Patent Application Ser. No. 63/319,927, entitled "NON-INVASIVE URINE MANAGEMENT SYSTEMS AND METHODS", filed on 15 Mar. 2022, which is hereby incorporated by reference as if set forth in full in this application for all purposes.

BACKGROUND

Non-invasive urine management systems have been developed for use in various populations, including people with incontinence, people with limited mobility, people who are largely or wholly bed-bound, and people in environments without ready access to normal bathroom facilities. However, currently available approaches suffer from at least one of the following problems:

- They are suitable for just females or just males;
- Devices are contoured to fit "average" body sizes and shapes;
- Device for females require externally applied pressure, for example from a rolled towel, to keep them in place;
- They entail significant cost in the required parts that are single-use, for hygiene;
- They involve relatively large area of direct contact with skin that may be sensitive and/or fragile;
- They require adhesive contact to be made and then broken from skin;
- They allow a high humidity environment to persist close to the skin for significant periods. The problem is exacerbated with devices for females, as they allow significant urine leakage in conditions of normal use.

There is, therefore, a need for improved methods and systems for non-invasive management systems using devices that may be used comfortably and safely, irrespective of the user's gender, or abdominal size and shape, over short or long periods. Ideally, the costs of initial outlay and ongoing operation, including for any disposable parts, would be low.

SUMMARY

The present invention includes devices and methods for non-invasive urine management.

In one embodiment, a device comprises: a sleeve comprising a waterproof layer attached to a water-permeable layer to form a cavity, the cavity being open at an upper perimeter and having a folded over antapex region forming a pocket; and a malleable framework comprising a top bar, first and second tubes, and a cup having a reservoir; wherein bottom ends of the first and second tubes are attached to the cup such that a continuous path for fluid flow exists between the cup reservoir, a lumen of the second tube, and a suction port at the top end of the second tube; wherein a first end of the top bar is attached to the top end of the first tube, closing off the lumen of the first tube at an attachment location; wherein an opposite end of the top bar is attached to a part of the second tube near the top end of the second tube, leaving the lumen of the second tube open; and wherein the sleeve is configured to enclose at least a lower portion of the framework, such that the cup fits into the pocket, with lower portions of the first and second tubes lying within the sleeve cavity.

In another embodiment, a device comprises: a sleeve comprising a waterproof layer attached to a water-permeable layer to form a cavity, the cavity being open at an upper perimeter and having a folded over antapex region forming a pocket; and a malleable framework comprising a top bar, first and second side bars, a tube and a cup having a reservoir. One end of the top bar is attached to a top end of the first side bar, an opposite end of the top bar is attached to a top end of the second side bar, and a bottom end of the tube is attached to the cup such that a continuous path for fluid flow exists between the cup reservoir and a suction port at a top end of the tube, through a lumen of the tube. The sleeve is configured to enclose at least a lower portion of the framework, such that the cup fits into the pocket and a lower portion of the tube lies within the cavity.

In yet another embodiment, a method of making a urine collection sleeve for a non-invasive urine management system comprises: attaching side edges of a water-permeable layer to side edges of a waterproof layer to form a cavity, open at an upper perimeter and at an antapex region; and attaching a lower portion of the waterproof layer, extending beyond a lower edge of the water-permeable layer and folded over a lower portion of the water-permeable layer, to the lower portion of the water-permeable layer, such that a pocket is formed at the antapex region.

A further understanding of the nature and the advantages of particular embodiments disclosed herein may be realized by reference to the remaining portions of the specification and the attached drawings.

DETAILED DESCRIPTION OF EMBODIMENTS

Described herein are embodiments of devices and methods for non-invasive urine management.

Taking a broad, high-level view, a device of the present invention at its simplest comprises (1) a malleable framework comprising hollow elements, configured such that a continuous path for fluid flow is formed through the elements, exiting the framework at a suction port, and (2) a sleeve comprising a waterproof layer attached to a water-permeable layer to form a cavity; wherein the sleeve is configured to enclose at least a lower portion of the framework. A method by which such a device may be used for non-invasive urine management comprises shaping the framework to roughly conform to the surface of the lower abdomen of the subject, inserting at least a lower part of the resulting curved framework into the sleeve, positioning the sleeved framework over the lower abdomen in such a way that one of the hollow elements is positioned to hold urine captured by the sleeve, and applying suction to the hollow elements to remove urine as desired.

The invention may best be understood, however, with reference to particular embodiments which will be described below and illustrated in the accompanying figures.

Figure 1:
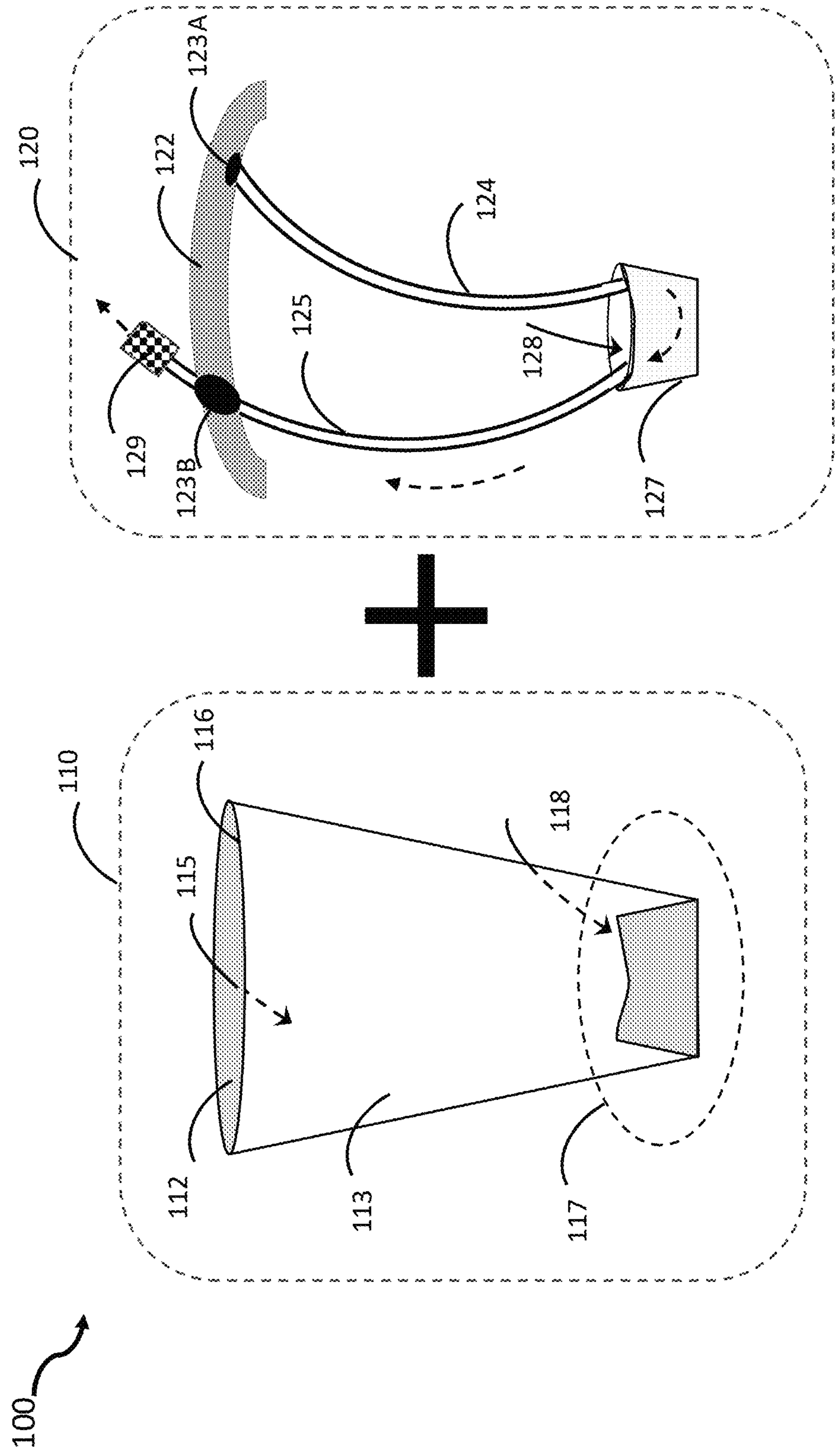
FIG. 1 illustrates parts of a device according to some embodiments of the present invention.

FIG. 1 shows a sleeve 110 and a malleable framework 120 that in combination make up a device 100 according to some embodiments of the present invention. Sleeve 110 comprises a waterproof layer 112 attached to a water-permeable layer 113 to form a cavity 115. The layers have shapes that are roughly triangular, being wider at top edges, and narrower at bottom edges. Cavity 115 has an open upper perimeter 116, and an antapex region 117, in which a lower portion of the water-permeable layer 113 is folded over to form a pocket 118 into which cup 127 (described below) can securely fit, Framework 120 comprises a top bar 122, first and second tubes 124 and 125, and a cup 127 having a reservoir 128. Bottom ends of the first and second tubes 124, 125 are attached to the cup such that a continuous path for fluid flow exists between the cup reservoir, a lumen of the second tube 125, and a suction port 129 at the top end of the second tube. A dashed arrow indicating part of the flow path for urine (and/or air) sucked through the tube are shown alongside the tubes, for simplicity, rather than within the tube lumens, where they would actually be.

A first end of the bar 122 is attached to the top end of the first tube, closing off the lumen of the first tube at an attachment location 123A. An opposite end of bar 122 is attached to a part of the second tube at an attachment location 123B near the top end of the second tube, without closing off the lumen of the second tube. This may be achieved by an external sealing ring, for example.

The relative shapes and sizes of the sleeve and the framework are designed such that at least a lower portion of the framework fits easily into the sleeve, with the cup fitting into the cup-shaped pocket, and lower portions of the first and second tubes lying within the sleeve cavity. In the embodiment shown in FIG. 1, almost the entire framework 120, with the possible exception of the suction port, would be enclosed by sleeve 110, but the drawings are not to scale, and certainly should not be taken to limit the possible variations in shape and size that are encompassed by the present invention.

Notice that the top bar, tubes and cup of the framework are malleable, such that they can be readily but reversibly shaped, for example by manual bending, to curve and form the framework into a non-planar, roughly triangular shape. Materials having an appropriate degree of “shape memory” may be particularly useful in this regard. The target is to shape the top bar to lie comfortably against and laterally across the abdomen of the subject (with only the thickness of part of the sleeve between the bar and the skin), to shape the tubes to extend down towards the perineal region, following the natural body topography from the abdomen towards the legs, and to position the cup so it may be held comfortably in the intergluteal cleft. When used on the subject, the cup can then collect urine directed there in part by the sleeve.

Figure 2:
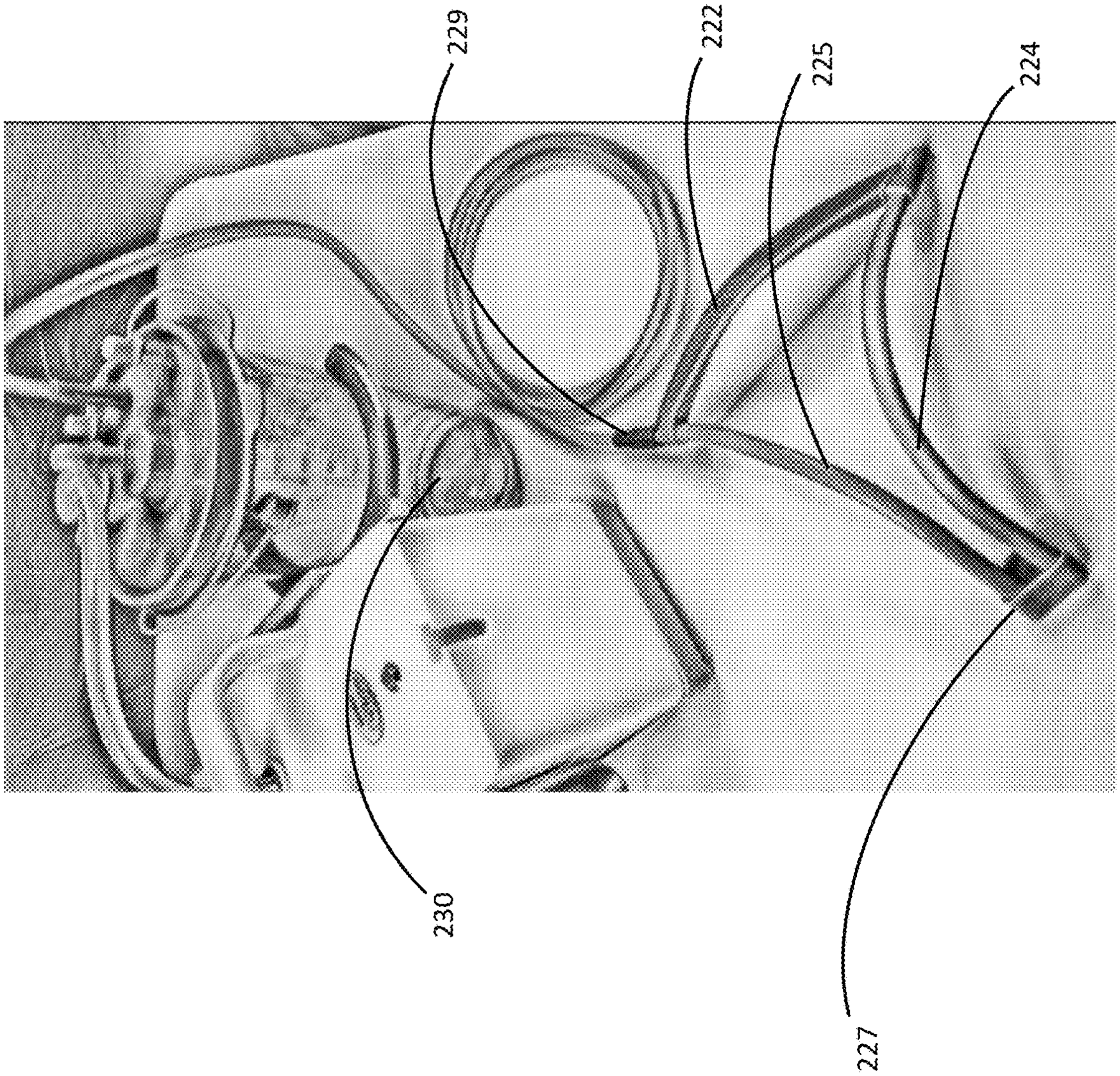
FIG. 2 is an image of a framework of a device according to a first set of embodiments.

FIG. 2 is a captured image of an experimental framework according to some embodiments of the present invention, showing top bar 222, tubes 224 and 225, feeding into cup 227, and suction port 229 connected to a vacuum-extraction system, including reservoir 230. The figure shows the framework during a demonstration of some aspects of device operation. In particular, the continuous fluid flow path is seen, from the sealed top end of tube 224, down through the reservoir of cup 227, and up through the other tube 225 to the suction port 229. When the framework is being used (in conjunction with the sleeve to be described below) on a subject, any urine captured in cup 227 can therefore be sucked out of cup 227, through tube 225 and suction port 229 to exit the framework, and to be collected by reservoir 230 for subsequent disposal.

In some embodiments, the bar and cup are formed by injection molding processes, while the tubes are formed by a co-extrusion process that creates the channels for reinforcing metallic wires at the same time as the main tube lumen for fluid flow. In some other embodiments, the material of the tubes is standard medical grade PVC tubing material with the addition of side reinforcements in the form of coated copper wires, and the cup is also made of PVC. Many other materials, including silicone rubber, may be used in these framework components.

Now consider the roughly conical sleeve 110, into which all or at least a significant lower portion of framework 120 can be inserted. The materials of which the sleeve 110 is made may be chosen from a wide variety of readily available fabrics. The water-permeable layer 113 is required to both absorb urine and wick urine away from the surface of incidence through to the opposite surface (which faces the waterproof layer), dispersing the urine laterally through the layer if necessary. These objectives may be achieved, for example, by a polypropylene spunbond non-woven layer incorporating a small amount of a non-wetting agent. Many other choices may be made. In some embodiments, multiple sub-layers of the same or different materials may be used to make up the water-permeable layer.

The waterproof layer 112 is typically a simple plastic film, such as polyethylene film, of a type often used as an outer layer in sanitary pads or diapers.

Figure 3:
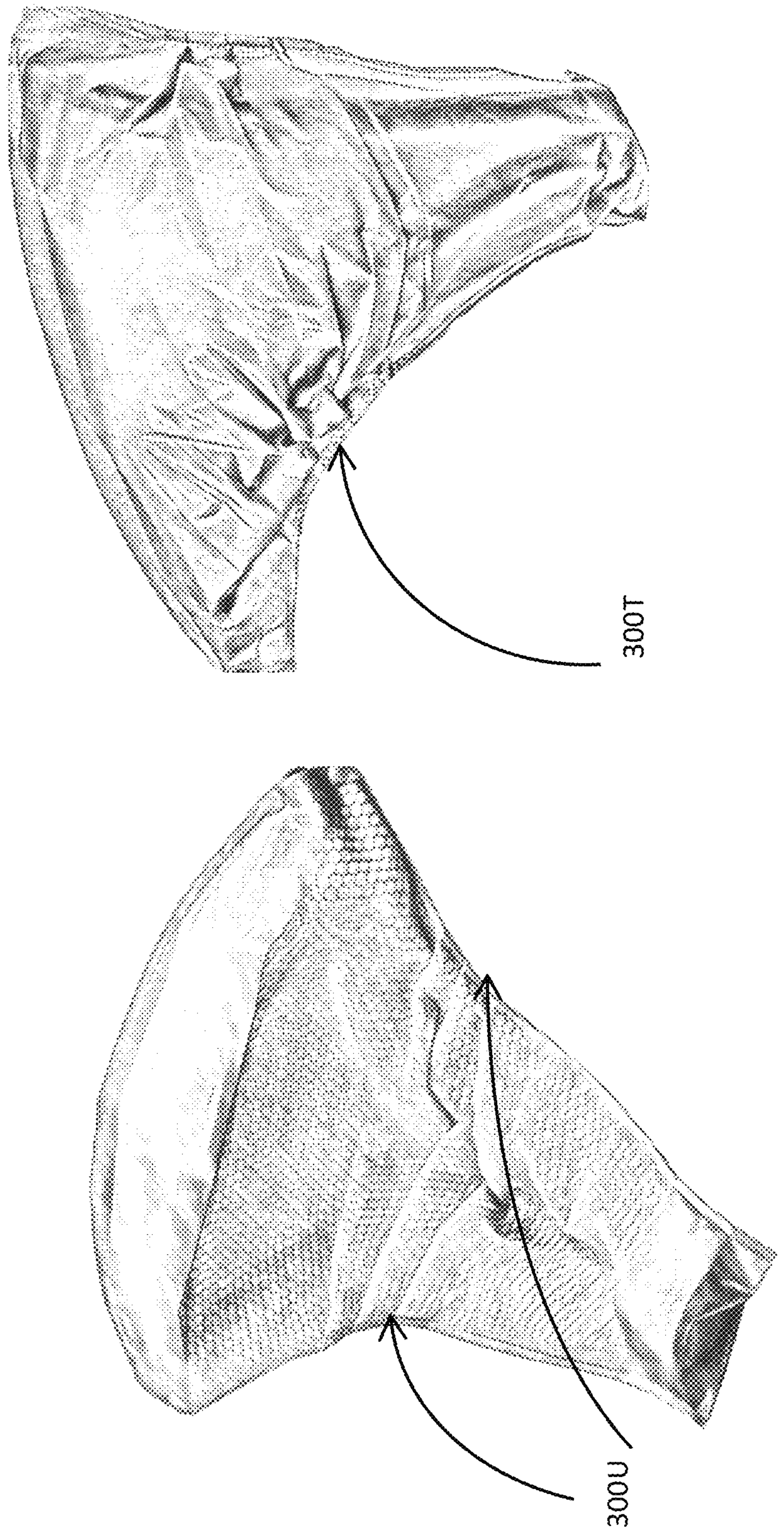
FIG. 3 illustrates pleating in a sleeve according to some embodiments.

In some embodiments, the sleeve is fabricated with pleating in the side edge attachments between the water-permeable and waterproof layers, like the pleating found in many types of surgical face masks. In the latter case, the pleating allows the mask to curve comfortably over the lower part of the face, providing breathing space for the wearer while maintaining skin contact around the edges to minimize gas flow in or out. In the present invention, the pleating allows the sleeve with its inserted framework to similarly curve over the lower regions of the wearer, providing some space for comfort, while maintaining closer contact around the edges to minimize the possibility of urine leakage. The left-hand image in FIG. 3 shows the sleeve underside—the largely concave surface of a water permeable layer adjacent the skin when in use—and the right-hand image shows the sleeve top side—the largely convex surface facing outwards from the subject when in use. Pleats have been formed along two side edges of the sleeve, some indicated in the left-hand image as 300U and some in the right-hand image as 300T.

Methods of using devices of the present invention may usefully be considered in terms of comprising four steps. The first step is to manually shape and position the framework, which will generally be provided to the user—generally some type of nurse or care-giver—with some initial curvatures likely to suit an “average” body, (or possibly an average within a size category such as small, medium, large and extra-large) on the receiving person, such that the bar lies over and across an upper part of the person’s abdomen, the two tubes curve down towards their meeting point in the cup in the area of the person’s perineum, and the cup is then positioned to be held reasonably comfortably in the person’s intergluteal cleft. No part of the framework is inserted into the body. The framework is designed to fit most comfortably around a seated person, but it may also be useful for a person lying on their back or side.

The second step, after the framework has been made to fit snugly and comfortably around the person's body, is to remove the framework from the person and insert the framework into the sleeve, so that at least a lower portion of the framework up to the bar, and preferably the whole framework except for the suction port, is enclosed. The cup is positioned neatly into the pocket at the base, and at least the lower portions of the two tubes fit within the sleeve cavity, lying along the inner side edges. The left-hand image in FIG. 3 shows a typical arrangement in which almost the entire framework has been placed within the sleeve, the only visible portion protruding outside it being the suction port at the upper right corner of the sleeve. The cup is of course completely hidden from view, but the folded over region behind which the cup sits is indicated by the dashed oval.

The third step is to place the suitably curved and now wholly or partly sleeve-enclosed framework on the person such that edges of the water-permeable layer lining the cavity of the sleeve are in skin contact with the person's abdomen, while the bar lies over and across an upper part of the person's abdomen, the two tubes extending down within the sleeve towards the person's perineum, and the sleeve pocketed cup being held in the subject's intergluteal cleft. Small adjustments to the curvature of the bars and tubes may be carried out if needed. No part of the device (framework or sleeve) is inserted into the person's body.

In most cases, as discussed above, the entire framework except for the suction port at the top of one tube will be enclosed in the sleeve, with the only protrusion being the suction port. This is likely to be the most comfortable arrangement for the subject, but the device should still be operable with the bar and even upper portions of the tubes protruding above the open upper perimeter of the sleeve if necessary.

The fourth step is to connect the suction port to a vacuum line leading through a urine reservoir to a vacuum pump. See FIG. 2, illustrating device operation where merely for the purpose of a simple demonstration, the sleeve has been removed, revealing only the framework.

Hospitals and nursing homes typically have ready access to vacuum system access ports and urine collection reservoirs. In other situations, an inexpensive portable pump may be used, some being commercially produced with a suitable in-line collection reservoir. Before the vacuum is applied, urine passed by the person encounters the water-permeably layer of the sleeve and is either held there, or wicked away through the layer thickness, either to the cup reservoir (possibly with some help from gravity), or to the waterproof layer surface where it is stopped and may flow down to the cup reservoir. When the vacuum is applied, urine is immediately sucked out of the cup reservoir up through one tube (tube 125 in FIG. 1, tube 225 in FIG. 2) into the external urine collection reservoir (230 in FIG. 2), causing any urine present in or between the sleeve layers to be very actively pulled down into the cup, and then sucked out through the tube, and so on. Experiments have shown this to be highly effective in removing significant volumes of liquid very quickly, restoring the layers of the sleeve to dryness, and maintaining that dryness over long periods.

The fluid flow path between the cup reservoir and through tube 125 up to the suction port is essentially water-tight, but not completely air-tight. due to slightly gas permeable tubing and seals at attachment points between components of the framework, However, rather than being a problem, this actually benefits device operation, as when a vacuum is applied at the suction port, pulling liquid from the cup reservoir up through one tube, air is simultaneously sucked out, some of it from the other, "empty" tube, but also some from the air space between the sleeve and the skin, and around the cup. This suction helps to hold the edges of the sleeve securely against the subject's skin, which minimizes the possibility of urine leakage. It also has a cooling effect on the skin and reduces skin-to-skin contact at these edge areas, which are otherwise prime sites for trapping moisture, from urine or sweat. Trapped moisture and/or surface rubbing can cause soreness and even skin breakdown.

The four method steps described above apply for a single session of device use. Of course, after some time, of the order of several hours, the suction port may need to be temporarily disconnected so that the device may be removed, allowing the sleeve to be disposed of, for good hygiene, and a fresh unused sleeve obtained. Possibly the urine collection reservoir will need attention. Then the method may be repeated, as desired.

It should be noted that the relatively simple sleeve, the disposable part of the device, the sleeve, can be made at a significantly lower cost than can the disposable parts (catheters, plugs etc.) of other urine management systems in current use. In some embodiments, the method of making a sleeve for a non-invasive urine management device of the present invention comprises just two essential steps. The first step is attaching side edges of a roughly triangular shaped absorbent layer to side edges of a roughly triangular shaped waterproof layer to form a roughly conical cavity, open at a wide upper perimeter and a narrow antapex region. The second step is attaching a lower portion of the waterproof layer, extending beyond a lower edge of the absorbent layer, to the absorbent layer to form a waterproof cup-shaped cavity at the antapex, completing the sleeve.

In some embodiments, pleats are formed during the first step of the method, allowing the two attached layers to bulge into a curved shape when placed on the body, following the convexity of the human pelvic region. This approach to making fabric devices that can be packed flat but then easily shaped into curved 3-dimensional shapes is well known in other applications, such as in the making of face masks, which can accommodate a wide variety of face sizes and shapes.

In some embodiments, the machinery used to make the sleeves is adapted from machinery used to make face masks. In some cases, this machinery may leave a small opening at the folded over edge of the waterproof layer at the narrow antapex region of the sleeve, but this does not affect device function.

Figure 4:
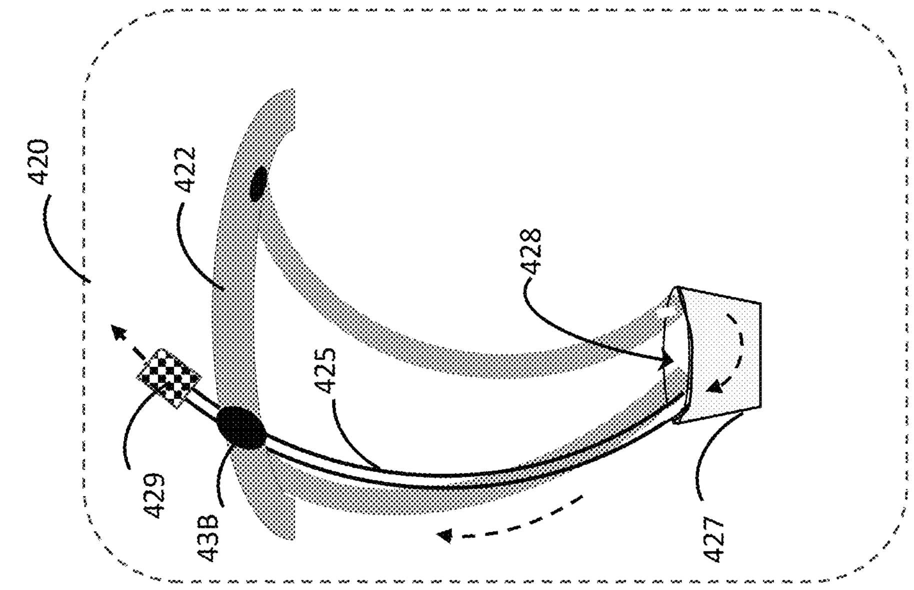
FIG. 4 illustrates a framework of a device according to a second set of embodiments.

In the device embodiments discussed above, the framework includes two tubes, attached to a top bar, with the tubes not only providing lumens through which fluid may flow, but also providing structural support. In another set of device embodiments, such as that illustrated in FIG. 4, the non-planar framework 420) simply uses a solid (though malleable) material to provide the triangular structural support (422), along with a single tube (425) with a lower end attached to a cup (427) and an upper end attached to support 422 at location 438, so that fluid may be pulled out of the cup reservoir (428), travel up the tube to a suction port (429), and then be removed by a vacuum-extraction system (not shown). The operation of these embodiments is basically the same as that of the "two-tube" set of embodiments, with the difference being that no suction is applied to the side bars of the framework, but only to the lumen of the single tube. Air and urine may still be drawn from the cup through the single tube present, additional urine may be drawn from the permeable layer and cavity of the sleeve into the cup, to be sucked up, and so on. The devices to a large degree offer the same advantages as those discussed above with respect to "two-tube" embodiments, those of drawing air from spaces between the sleeve and the skin and around the cup, keeping the sleeve edges in place, cooling the skin, and reducing skin-to-skin contact.

Embodiments of the present invention offer many advantages over prior art in the field of urinary management. All the component parts can be made of inexpensive, safe, readily available materials, the parts can be made and assembled using well established fabrication techniques, the disposable components can be provided at relatively low cost, and the framework is intentionally designed and fabricated to be reusable, lowering the effective cost of use of the device over time. The devices are equally well suited to males and females, comfortably fitting a wide variety of individuals' shapes and sizes while making limited, soft skin contact over limited areas, including the skin folds of the pelvic region, without adhesives. Urine removal can be performed continuously and non-invasively, with applied suction creating air flow that cools the skin, while holding the device in place despite natural movements by the wearer, and while minimizing problematic skin-to-skin rubbing and moisture trapping. This last advantage is particularly helpful in devices intended for the female anatomy.

Although the description has been described with respect to particular embodiments thereof, these particular embodiments are merely illustrative, and not restrictive.

It will also be appreciated that one or more of the elements depicted in the drawings/figures may be implemented in a more separated or integrated manner, in accordance with a particular application.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

The invention claimed is:

1. A device comprising:

a sleeve comprising a waterproof layer attached to a water-permeable layer to form a cavity, the cavity being open at an upper perimeter and having a folded over antapex region forming a pocket; and a malleable framework comprising a top bar, first and second tubes, and a cup having a reservoir;

wherein bottom ends of the first and second tubes are attached to the cup such that a continuous path for fluid flow exists between the cup reservoir, a lumen of the second tube, and a suction port at a top end of the second tube;

wherein a first end of the top bar is attached to the top end of the first tube, closing off the lumen of the first tube at an attachment location;

wherein an opposite end of the top bar is attached to a part of the second tube near the top end of the second tube, leaving the lumen of the second tube open; and wherein the sleeve is configured to enclose at least a lower portion of the framework, such that the cup fits into the pocket, with lower portions of the first and second tubes lying within the sleeve cavity.

2. The device of claim 1, wherein pleats formed during the attachment of waterproof and water-permeable layers of the sleeve allow the sleeve to reversibly assume any one of a range of curved 3D configurations according to a corresponding degree of pleat unfolding.

3. The device of claim 1, wherein the water-permeable layer of the sleeve comprises a wicking fabric, configured to efficiently transport urine from a water-permeable layer surface on which the urine is incident to an opposing water-permeable layer surface facing the waterproof layer.

4. The device of claim 1, wherein the water-permeable layer comprises a plurality of sublayers.

5. The device of claim 1, wherein the first and second tubes of the framework comprise standard medical grade PVC tubing with side reinforcement from polypropylene-coated copper wire.

6. The device of frame 1, wherein the top bar and the first and second tubes of the framework are characterized by having shape memory, such that after being shaped into a first 3D configuration, the framework will tend to remain in the first 3D configuration until it is reshaped by hand or by a movement of an individual around which the framework is positioned.

7. The device of claim 1, wherein the sleeve is disposable, intended for a single use; and wherein the malleable framework is durable, intended for reuse.

8. A device comprising:

a sleeve comprising a waterproof layer attached to a water-permeable layer to form a cavity, the cavity being open at an upper perimeter and having a folded over antapex region forming a pocket; and a malleable framework comprising:

a top bar, first and second side bars, a tube and a cup having a reservoir;

wherein one end of the top bar is attached to a top end of the first side bar, an opposite end of the top bar is attached to a top end of the second side bar, and a bottom end of the tube is attached to the cup such that a continuous path for fluid flow exists between the cup reservoir and a suction port at a top end of the tube, through a lumen of the tube; and wherein the sleeve is configured to enclose at least a lower portion of the framework, such that the cup fits into the pocket and a lower portion of the tube lies within the cavity.

9. The device of claim 8, wherein pleats formed during the attachment of waterproof and water-permeable layers of the sleeve allow the sleeve to reversibly assume any one of a range of curved 3D configurations according to a corresponding degree of pleat unfolding.

10. The device of claim 8, wherein the water-permeable layer of the sleeve comprises a wicking fabric, configured to efficiently transport urine from a water-permeable layer surface on which the urine is incident to an opposing water-permeable layer surface facing the waterproof layer.

11. The device of claim 8, wherein the water-permeable layer comprises a plurality of sublayers.

12. The device of claim 8, wherein the tube comprises standard medical grade PVC tubing with side reinforcement from polypropylene-coated copper wire.

13. The device of claim 8, wherein the top bar, side bars, and tube of the framework are characterized by having shape memory, such that after being shaped into a first 3D configuration, the framework will tend to remain in the first 3D configuration until it is reshaped by hand or by a movement of an individual around which the framework is positioned.

14. The device of claim 8, wherein the sleeve is disposable, intended for a single use; and wherein the malleable framework is durable, intended for reuse.

* * * * *